United States Patent [19]
Danielson et al.

[11] Patent Number: 5,527,709
[45] Date of Patent: Jun. 18, 1996

[54] IMMUNOASSAYS WITH LABELED THYRONINE HAPTEN ANALOGUES

[75] Inventors: Susan J. Danielson; Barbara A. Brummond, both of Rochester; Patricia N. Tyminski, Webster; Ignazio S. Ponticello, Pittsford, all of N.Y.

[73] Assignee: Johnson & Johnson Clinical Diagnostics, Inc., Rochester, N.Y.

[21] Appl. No.: 410,548

[22] Filed: Mar. 23, 1995

Related U.S. Application Data

[63] Continuation of Ser. No. 151,582, Nov. 12, 1993, abandoned, which is a continuation of Ser. No. 904,614, Jun. 26, 1992, abandoned.

[51] Int. Cl.⁶ .................................................. G01N 33/545
[52] U.S. Cl. ........................... 436/500; 435/7.93; 436/817
[58] Field of Search ........................... 435/7.93; 436/500, 436/544, 817

[56] References Cited

U.S. PATENT DOCUMENTS

| | | | |
|---|---|---|---|
| 2,761,417 | 9/1956 | Russell et al. | 118/410 |
| 4,089,747 | 5/1978 | Bruschi | 195/99 |
| 4,258,001 | 3/1981 | Pierce et al. | 422/56 |
| 4,430,436 | 2/1984 | Koyama et al. | 436/531 |
| 4,670,381 | 6/1987 | Frickey et al. | 435/007 |
| 4,760,142 | 7/1988 | Primes et al. | 544/287 |
| 4,786,591 | 11/1988 | Draeger et al. | 435/7 |

FOREIGN PATENT DOCUMENTS 0078952  3/1983  European Pat. Off. .

OTHER PUBLICATIONS

Kabakoff in Enzyme-immunoassay CRC Press (1980) pp. 71–104.
Erlanger Meth. Enz. 70 (1980) pp. 85–104.
Harlow et al. *Antibodies A Laboratory Manual* Cold Spring Harbor Laboratory (1988) pp. 584–587.

*Primary Examiner*—Mary E. Ceperley

[57] ABSTRACT

The invention is directed to an immunoassay for a thyronine derivative comprising:

A. contacting a liquid sample, containing a thyronine derivative, with a labeled thyronine hapten analogue of the derivative in the presence of antibodies for the thyronine derivative under conditions that promote the formation of antibody-thyronine immunocomplexes; and B. determining the bound or unbound quantity of the thyronine derivative in the liquid; characterized in that the labeled thyronine derivative comprises:

(i) a label, of the type used in immunoassays, having an amine or sulfhydyl group;
 (ii) a thyronine nucleus and
 (iii) a linking chain linking the label to the thyronine nucleus.

9 Claims, No Drawings

IMMUNOASSAYS WITH LABELED THYRONINE HAPTEN ANALOGUES

This application is a continuation of U.S. application Ser. No. 08/151,582, filed Nov. 12, 1993, now abandoned, which is a continuation of U.S. application Ser. No. 07/904,614, filed Jun. 26, 1992, now abandoned.

FIELD OF THE INVENTION

This invention relates to clinical chemistry particularly immunoassays.

BACKGROUND OF THE INVENTION

Immunoassays, which take advantage of natural immunological reactions, have found wide-spread use as analytical techniques in clinical chemistry. Because of the specificity of the reactions, they are particularly advantageous in quantifying biological analytes that are present in very low concentration in biological fluids. Such analytes (called ligands herein) include, for example, antibodies, therapeutic drugs, narcotics, enzymes, hormones, proteins, etc.

In competitive binding immunoassays, a labeled hapten analogue is placed in competition with unlabeled haptens for reaction with a fixed amount of the appropriate antibody. Unknown concentrations of the hapten can be determined from the measured signal of either the bound or unbound (i.e. free) labeled hapten analogue.

Conventional labels include radioactive tags, enzymes, chromophores, fluorophores, stable free radicals, and enzyme cofactors, inhibitors and allosteric effectors.

In competitive immunoassays for thyronines, such as thyroxine, specific requirements for labeled thyronine hapten analogues (hereafter sometimes LDH) include: 1) at least 60% of the LDH can be bound by excess immobilized antibody; 2) affinity of the LDH for immobilized antibody is such that competition of a fixed amount of LDH with the drug occurs in a therapeutically relevant concentration range; 3) the process used to prepare the LDH requires only a few steps and 4) stability of the LDH against hydrolysis of its enzyme label under storage conditions. Requirements imposed on the thyronine hapten analogues include: 1) accessibility of the analogue to the immobilized antibody following conjugation with the enzyme label; 2) specific recognition of the labeled analogue by the antibody to the drug; and 3) sufficient reactivity of the drug analogue with the enzyme label, either directly or following activation of the enzyme or analogue, under conditions that do not adversely affect enzyme activity.

U.S. Pat. No. 4,786,591 discloses haptens comprising a thyroxine (T4) nucleus having an active ester group. The problem is that these haptens do not provide labeled hapten analogues that are at least 60% immunoreactive.

SUMMARY OF THE INVENTION

The present invention provides an immunoassay for a thyronine derivative comprising:

A. contacting a liquid sample, containing a thyronine derivative, with a labeled thyronine hapten analogue of the derivative in the presence of antibodies for the thyronine derivative under conditions that promote the formation of antibody-thyronine immunocomplexes; and B. determining the bound or unbound quantity of the thyronine derivative in the liquid; characterized in that the labeled thyronine derivative comprises:

(1) a label, of the type used in immunoassays, having an amine or sulfhydryl group;

(2) a thyronine nucleus; and (3) a linking chain, linking the thyronine nucleus to the label through (i) the amino or the carboxyl group of the thyronine nucleus and (ii) the amine or sulfhydryl group of the label, having therein from 4 to about 22 chain atoms, including (iii) at least one ring group selected from 1,4-piperazinylene, 2,5-dimethyl-l,4-piperazinylene; 1,3-imidazolidinylene; and 1,3-hexahydrodiazepinylene; and (iv) one or more $C_1$ to $C_6$ alkylene groups; wherein the groups (iii) and (iv) are interconnected to each other through one or more groups selected from —O—, —S—, imino, amide, carboxyl and carbonyl.

The analogues of the present invention include those having structure 1 as follows:

Structure 1

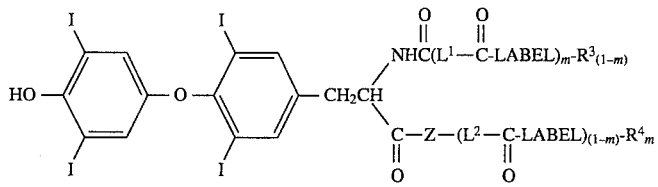

wherein —Z— is selected from 1,4-piperazinylene, 2,5-dimethyl- 1,4-piperazinylene, 1,3-imidazolidinylene, 1,3-hexahydrodiazepinylene, 1,4-piperazinylenecarbonyl, 2,5-dimethyl-1,4-piperazinylenecarbonyl; 1,3-imidazolidinylenecarbonyl, 1,3-hexahrdrodiazepinylenecarbonyl, oxa (—O—), thia (—S—), imino (—$NR^1$—) in which $R^1$ is hydrogen or alkyl of about 1 to 6 carbon atoms;

$L^1$ and $L^2$ each represent a linking chain having therein from 4 to about 22 chain atoms, including (i) together with Z, at least one ring group selected from 1,4-piperazinylene; 2,5-dimethyl-1,4-piperazinylene; 1,3-imidazolidinylene; and 1,3-hexahydrodiazepinylene; and (ii) one or more $C_1$ to $C_6$ alkylene groups; wherein the groups (i) and (ii) are interconnected to each other through one or more groups selected from —O—, —S—, imino, carbonyl, amide (—$OCNR^1$— and —$NR^1CO$—), and ester (—COO— and —OCO—);

$R^3$ represents alkyl, hydroxyalkyl, or alkoxy of about 1 to 10 carbon atoms; and $R^4$ is alkyl of about 1 to 10 carbon atoms; and m is 0 or 1.

Thyroxine is an example of the thyronines that can be assayed using this invention. The labeled thyronine hapten analogues used in the immunoassay are reproducible Y greater than 60% immunoreactive. The labels have good washout properties. Thus they have low nonspecific binding due to relatively low substitution ratios. Also the structure of the linking group has a positive affect on the shape of the dose response obtained and thus the performance of a thyronine assay. This positive affect results from a greater rate of change of the amount of the bound labeled analogue over the desired measuring range of thyronine.

DETAILS OF THE INVENTION

The labeled thyronine hapten analogues are the subject of copending U.S. Ser. No. 904,617, abandoned, titled IMMUNOASSAYS WITH LABELED THYRONINE HAPTEN ANALOGUES in the name of Danielson et al. filed on the same date as the present case. Thyronine hapten analogues, from which the labels are made are the subject of copending U.S. Ser. No. 904,616, abandoned, titled THYRONINE HAPTEN ANALOGUES FOR IMMUNOASSAYS in the name of Danielson et al also filed on the same day as the present case.

Methods of making the thyronine hapten analogues are presented below.

There are two convenient reactive sites on the thyroxine which allow appendage of a linking chain followed by a reactive active ester group in the case of the new haptens of this invention, or followed by an enzyme moiety in place of the active ester group when making the new labels resulting from the invention. The two convenient sites are the primary amine and the carboxylic acid groups. Whichever site is chosen, the other site is first blocked to prevent interference with subsequent reactions employed to sequentially build the desired linking chain and terminate it with an active ester group and finally with an enzyme to produce the desired label.

Preferably the linking chain is appended from the primary amine group and the first step in the preparation is to block the carboxylic acid group. This can be accomplished by converting the free acid to an ester with a conventional esterification reaction such as condensation of the acid with an alcohol, preferably methanol with either an acid or base catalyst and separating the ester, e.g., the methyl ester. Subsequently, the amine is condensed with a dicarboxylic acid anhydride to form an amide linkage by conventional amide-forming condensation techniques, and then the carboxylic acid is either condensed with an N-hydroxyimide such as N-hydroxysuccinimide to form the active ester hapten, or preferably, the linking chain is extended further by sequential condensations of either a diamine having one of the two amine groups protected (blocked), or an aminoalcohol with the new terminal carboxy group and continuing by deblocking the amine and condensation of a dicarboxylic acid anhydride with the new terminal deblocked amine, or hydroxy group. These condensations are sequentially continued until the desired chain length is achieved. The diamines employed preferably have one amine group protected (blocked) with conventional blocking groups such as butoxycarbonyl (BOC) or benzyloxycarbonyl groups. Thus, after addition of each protected diamine onto the linking chain, a deblocking step, e.g., removal of the BOC or benzyloxycarbonyl group with trifluoracetic acid and HBr/ HOAc respectively, is required before extending the chain with the next dicarboxylic acid anhydride.

In accordance with this invention, at least one cyclic diamine of the structure

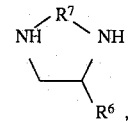

where $R^6$ is hydrogen or methyl and $R^7$ is an alkylene or methyl-substituted alkylene of 1 to 3 carbon atoms, such as methylene, ethylene, propylene and trimethylene, preferably the cyclic diamine is piperazine, is necessarily blocked and incorporated into the linking chain as described for the diamines. The final step in the preparation of the new thyronine hapten analogues is condensation of a terminal carboxy group with N-hydroxyimide as described before to produce the reactive active ester. The new active ester is condensed with an amino or sulfhydryl group-containing enzyme to produce the labelled thyronine hapten analogues.

Alternatively, the primary amine group on the thyronine can first be blocked, for example with the amine blocking groups described above and the linking group can be the appended to the carboxylic acid group on the thyronine moiety using the condensation, blocking, and deblocking reactions described hereinbefore in the desired sequence.

Intermediate Preparation 1:

Preparation of N-[4-(3-Succinimidoxycarbonylpropionyl)piperazinocarbonylmethoxyacetyl]thyroxine Methyl Ester

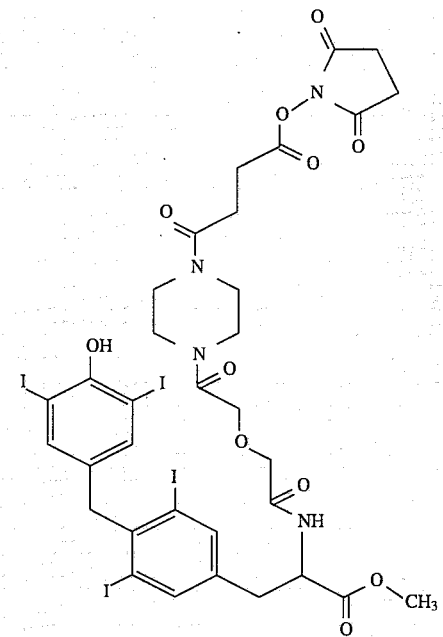

Step 1 Methyl Ester of Thyroxine

To a mixture of thyroxine (37 g, 0.047 mole) in methanol (500 mL) was added anhydrous hydrochloric acid gas. After a few minutes the slurry clears and the addition of HCl is continued for 30 minutes while the mixture is cooled in an ice/water bath. Stirring is continued for 2 hours while maintaining the temperature at 0°–10° C. The white solid was filtered and the filtrate concentrated to about 100 mL and placed in the freezer overnight, filtered, sucked dry, and combined with the previous material to give 39 g. The solid was dissolved in N,N-Dimethylformamide (100 mL) and added slowly to sodium bicarbonate (27 g) in water (1500 mL) while stirring. The mixture was stirred for an additional hour, extracted with ethyl acetate (5×200 mL), the combined organic solutions were washed with saturated NaCl solution (200 mL), dried over anhydrous magnesium sulfate, filtered, and the solution concentrated to 400 mL. To this solution was added petroleum ether 200 mL, the mixture was placed in the freezer for 16 hours and was then filtered to give 31.4 g.

$^1$H NMR (CDCl$_3$) δ 2.8 & 3.0(m, 2H, CH$_2$), 3.85 (mas, 4H, CH& CH$_3$), 7.1&7.7 (s,4H, aromatic H's).

Step2 N-(Carboxymethoxyacetyl)thyroxine Monomethyl Ester. Reaction of amine from step 1 with diglycolic anhydride A mixture of the thyroxine methyl ester (31.4 g, 0.04 mole) and diglycolic anhydride (11.6 g, 0.1 mole) in acetone (350 mL) was heated to 50°–60° C. in a hot water bath and then stirred to ambient temperature for 1 hour. The solvent was removed on a rotary evaporator in vacuo and to this residue was added chloroform (400 mL). The organic solution was washed with water (2×100 mL), washed with 5% HCl (2×100 mL), washed with saturated NaCl solution (100 mL), dried over anhydrous magnesium sulfate, filtered, and the solvent removed. To the residue was added chloroform (100 mL) and the solution was placed in the freezer overnight. The mixture was filtered to give 31.4 g; m.p. 157°–162° C.

$^1$H NMR(CDCl$_3$)δ 2.9 & 3.05(m,2H, T4—CH$_2$), 3.6(s, 3H, CH$_3$), 3.95(ABq, 2H, NHCOCH$_2$), 4.02(ABQ 2H CH$_2$CO),4.6(m, 1H, CH), 7.0&7.75(s,4H, aromatic H's), 8.25(d, 1H,NH), 9.1 (broad s, 1H, acid H)

Step 3 N-(Succinimidoxycarbonylmethoxyacetyl)-thyroxine Methyl Ester. Reaction of the acid from step 2 with N-hydroxysuccinimide A mixture of N-(carboxymethoxyacetyl)thyroxine monomethyl ester (27.2 g, 0.03 mole), N-hydroxysuccinimide (3.8 g, 0.033 mole), and N,N'-dicyclohexylcarbodimide (7.2 g, 0.033 mole) in acetone (200 mL) was stirred at room temperature for 20 hours. The mixture was filtered and chloroform (300 mL) was added. The organic solution was washed with water (3×100 mL), saturated NaCl solution (100 mL), dried over anhydrous magnesium sulfate, filtered, and the solvent removed on a rotary evaporator under vacuo to give 30 g. This material was used directly in the next step without further purification.

$^1$H NMR(CDCl$_3$) δ 2.85(s, 4H, CH$_2$CH$_2$), 3.05(m, 2H,Ar—CH $_2$),3.8(s,3H,CH$_3$), 4.2(ABq, 2H,NHCOCH$_2$), 4.58(ABq, 2H, CH$_2$CO), 4.85(m, 1H, CH), 7.1&7.65(2s,4H, Ar H's) Step 4 N-[4-(Benzyloxycarbonyl)piperazinocarbonylmethoxyacetyl]thyroxine Methyl Ester. Reaction of reactive ester with benzyl 1-piperazinecarboxylate To N-(Succinimidoxycarbonylmethoxyacetyl)thyroxine methyl ester (5.1 g, 0.005 mole) in chloroform (200 mL) was added dropwise over 10 minutes benzyl 1-piperazinecarboxylate (1.5 g, 0.0068 mole). The mixture was heated to 50°–60° C. with a hot water bath for 15 minutes and then stirred at ambient temperature for 16 hours. The mixture was washed with 5% HCl solution (2×100 mL), water (2×100 mL), saturated. NaCl solution (100 mL), dried over anhydrous magnesium sulfate, filtered, and the solvent removed. The residue was chromatographed on SiO$_2$ to give a solid.

$^1$H NMR(CDCl$_3$) δ 3.1 (m, 2H, Ar—CH$_2$), 3.25–3.7 (m, 8H, pip H's), 3.75(s,3H, CH$_3$), 4.1(ABq, 2H, NHCOCH$_2$), 4.3(ABq, 2H, CH$_2$COpip), 4.82(m, 1H,CH), 5.15(s,2H, OCH$_2$Ph), 7.05& 7.7 (2s,4H, Ar H's), 8.1 (d, 1H,NH).

Step 5 N-(Piperazinocarbonylmethoxyacetyl]thyroxine Methyl Ester Hydrobromide. Treatment of protected amine from step 4 with 30% HBr/HOAc N-[4-(Benzyloxycarbonyl)piperazinocarbonylmethoxyacetyl]thyroxine methyl ester from step 4 (11.0 g, 0.01 mole) and 30–35% hydrogen bromideacetic acid solution (80 mL) were stirred at room temperature for 1 hour. The mixture was then poured into ethyl acetate (1.0 L), stirred for 1 hour, filtered, and the solid washed with ethyl acetate (500 mL). The solid was then dried in a vacuum oven overnight at 45°–50° C. which was used without further purification in the next step.

Step 6 N-[4-(3-Carboxypropionyl)piperazinocarbonylmethoxyacetyl] thyroxine Monomethyl Ester. Reaction of amine hydrobromide from step 5 with succinic anhydride To N-(piperazinocarbonylmethoxyacetyl)thyroxine methyl ester Hydrobromide from step 5 (9.5 g, 0.01 mole) and succinic anhydride (2.0 g, 0.02 mole), in chloroform (400 mL) was added triethylamine (3.3 g, 0.033 mole). The slurry immediately begins to dissolve and the mixture was stirred overnight at room temperature. The next day the solid had all dissolved and the solution was washed with 5% HCl solution (3×100 mL), water (100 mL), saturated NaCl solution (100 mL), dried over anhydrous magnesium sulfate, filtered, and the solvent removed on a rotary evaporator in vacuo. This material was further purified by chromatography using SiO$_2$.

$^1$H NMR (CDCl$_3$) δ 2.6–2.8 (m, 4H, CH$_2$CH$_2$), 3.0–3.2(m, 2H, Ar—CH$_2$), 3.3–3.8(m, 8H, pip H's), 4.0(s,3H, CH$_3$), 4.1(ABq,2H, NHCOCH$_2$), 4.3(ABq, 2H,CH$_2$COpip), 4.85(m, 1H,CH), 7.1&7.7 (s,4H,Ar H's), 8.05(m, 1H,NH).

Step 7 N-[4-(3-Succinimidoxycarbonylpropionyl)piperazinocarbonylmethoxyacetyl]thyroxine Methyl Ester. Reaction of acid from step 6 with N-hydroxysuccinimide A mixture of N-[4-(3-carboxypropionyl)piperazinocarbonylmethoxyacetyl] thyroxine monomethyl ester from step 6 (4.3 g, 0.004 mole), N,N'-dicyclohexylcarbodiimide (0.824 g, 0.004 mole), and N-hydroxysuccinimide (0.46 g, 0.004 mole) in chloroform (70 mL) was stirred at room temperature for 20 hours and then heated to 50°–60° C. for 30 minutes. The reaction was cooled to 0°–5° C., filtered and to the filtrate was added chloroform (100 mL). The organic solution was washed with water (3×50 mL), saturated NaCl solution (50 mL), dried over anhydrous magnesium sulfate, filtered, and the solvent removed on a rotary evaporator under vacuo. A portion of the material was chromatographed to give pure material.

$^1$H NMR(CDCl$_3$) δ 2.8(m, 2H, pipCOCH$_2$CH$_2$), 2.82(s, 4H, CH$_2$CH$_2$), 2.95–3.2(m, 2H, CH$_2$CH$_2$CO$_2$), 3.3–3.8(m, 8H, pip H's), 3.8(s,3H,CH$_3$), 4.1 (ABq, 2H,NHCOCH$_2$), 4.3 ( ABq, 2 H, CH$_2$COpip), 4.85(m, 1H, CH), 7.1&7.7(S,4H, Ar H's), 8.1(m, 1H,NH).

Intermediate Preparation 2:

N-[4-(Succinimidoxycarbonylmethoxy-acetyl)piperazinocarbonylmethoxyacetyl] thyroxine Methyl Ester

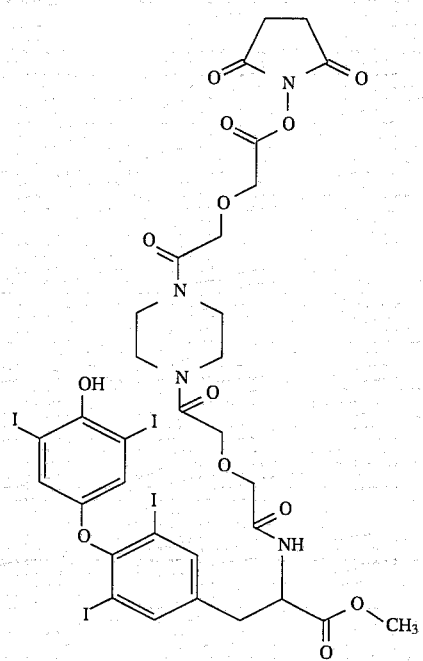

Step 1  N-(Piperazinocarbonylmethoxyacetyl)thyroxine Methyl Ester. Formation of free amine from amine hydrobromide from step 5, Intermediate Preparation 1

N-(Piperazinocarbonylmethoxyacetyl)thyroxine methyl ester hydrobromide from step 5. (3.6 g, 0.0034 mole) was dissolved in DMF (25 mL) and slowly poured into sodium bicarbonate (1.5 g, 0.017 mole) in water (200 mL) and stirred at room temperature for 1 hour. The aqueous slurry was extracted with chloroform(10×50 mL). The combined organic solution was washed with water (100 mL), saturated NaCl solution (100 mL), dried over anhydrous magnesium sulfate, filtered, and the solvent removed on a rotary evaporator under vacuo. This material was used directly in the next step.

Step 2  N-[4-(Carboxymethoxyacetyl)piperazinocarbonylmethoxyacetyl]thyroxine Monomethyl Ester. Reaction of free amine from step 1 with diglycolic anhydride N-(Piperazinocarbonylmethoxyacetyl)thyroxine methyl ester from step 1 (3.1 g, 0.0034 mole) and diglycolic anhydride (0.6 g, 0.0046 mole) in chloroform (200 mL) were heated to 50°–60° C. (hot water) and allowed to stir at ambient temperature for 16 hours. Chloroform (200 mL) was added. The mixture was washed with 5% HCl solution (2×100 mL), water (100 mL), saturated NaCl solution (100 mL), dried over anhydrous magnesium sulfate, filtered, and the solvent removed on a rotary evaporator in vacuo. This material was used directly in the next step.

$^1$H NMR(CDCl$_3$) δ 3.0–3.2(m, 2H, Ar—CH$_2$), 3.3–3.75(m 8H pip H's) 3.8(s 3H,CH$_3$),4.0–4.4(m, 8H 2×CH$_2$OCH$_2$), 4.85(m, 1H,CH), 7.1&7.7(s,4H, Ar H's), 8.0 (s, 1H,NH).

Step 3  N-[4-(Succinimidoxycarbonylmethoxy-acetyl)piperazinocarbonylmethoxyacetyl] thyroxine Methyl Ester. Reaction of acid from step 2 with N-hydroxysuccinimide A mixture of N-[4-(carboxymethoxyacetyl)piperazinocarbonylmethoxyacetyl] thyroxine monomethyl ester from step 2 (2.2 g, 0.002 mole), N,N'-dicyclohexylcarbodimide (0.52 g, 0.0025 mole), and N-hydroxysuccinimide (0.35 g, 0.003 mole) in chloroform (50 mL) was heated to 50°–60° C. (hot water) and then stirred at room temperature for 16 hours. The mixture was filtered and chloroform (100 mL) was added. The solution was washed with water (2×100 mL), 5% HCl solution (100 mL), saturated NaCl solution (100 mL), dried over anhydrous magnesium sulfate, filtered, and the solvent removed on a rotary evaporator under vacuo.

$^1$H NMR(CDCl$_3$)δ 2.85(s,4H, CH$_2$CH$_2$), 3.0–3.2(m, 2H, CH$_2$), 3.3–3.75 (m, 8H, pip H's), 3.8 (s, 3H, CH$_3$), 4.0–4.4 (m, 8H, 2×CH$_2$OCH$_2$), 4.82 (m, 1H,CH), 7.1&7.7(s,4H,Ar H's), 8.1(d, 1H,NH).

Intermediate Preparation 3:

Preparation of N-{3-[4-(3-succinimidoxycarbonylpropionyl)piperazinocarbonyl] propionyl}thyroxine Methyl Ester

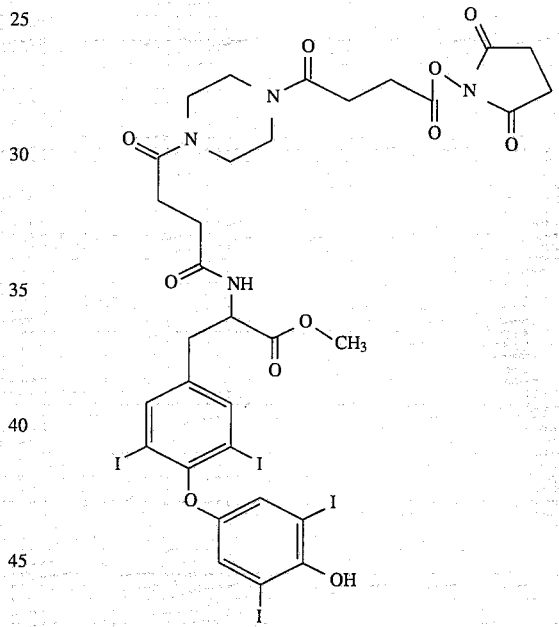

Step 1  N-(3-Carboxypropionyl)thyroxine Monomethyl Ester. Reaction of Thyroxine methyl ester of Intermediate Preparation 1 with succinic anhydride This material was prepared using the procedure outlined in Intermediate Preparation 1, step 2 except succinic anhydride was used in place of the diglycolic anhydride. The product was recrystalized from 1:1 acetone/acetonitrile.

$^1$H NMR (DMSO$_{d6}$)δ 2.3(m, 4H, CH$_2$CH$_2$), 2.78– 3.02, (m, 2H,ArCH$_2$), 3.6(s,3H,CH$_3$), 4.05(m, 1H,CH), 7.0&7.8(s,4H,Ar H's), 8.4(d, 1h,NH).

Step 2  N-(3-Succinimidoxycarbonylpropionyl)thyroxine Methyl Ester. Reaction of acid from step 1 with N-hydroxysuccinimide This material was prepared using the procedure outlined in Intermediate Preparation 1, step 3 except the acid N-(3-carboxypropionyl)thyroxine monomethyl ester from step 1 was used and this product was used directly in the next step without purification.

Step 3 N-[3-(4-Benzyloxycarbonylpiperazinocarbonyl)propionyl]thyroxine Methyl Ester. Reaction of reactive ester from step 2 with benzyl 1-piperazinecarboxylate This material was prepared using the procedure outlined in Intermediate Preparation 1, step 4 except the ester N-(3-succinimidoxycarbonylpropionyl)thyroxine methyl ester from step 2 was used. This material was purified by column chromatography (SiO$_2$).

$^1$H NMR (CDCl$_3$)δ 2.5–2.7(m, 4H, CH$_2$CH$_2$), 2.9–3.1 (m 2H, ArCH$_2$) 3.4–3.7 (m, 8H pip H's) 3.75(s,3H,CH$_3$), 4.8(m.1H,CH), 5.15(s,2H, ArCH$_2$O), 6.7(d, 1H,NH), 7.1&7.65(s,4H,Ar H's).

Step 4 N-(3-Piperazinocarbonylpropionyl)thyroxine Methyl Ester Hydrobromide. Treatment of protected amine from step 3 with 30% HBr/HOAc This material was prepared using the procedure outlined in Intermediate Preparation 1, step 5 except the protected amine N-[3-(4-benzyloxycarbonylpiperazinocarbonyl)propionyl]thyroxine methyl ester of step 3 was used to give a cream colored solid.

Step 5 N-{3-[4-(3-Carboxypropionyl)piperazinocarbonyl]propionyl}thyroxine Monoethyl Ester. Reaction of the amine hydrobromide from step 4 with succinic anhydride This material was prepared using the procedure outlined in Intermediate Preparation 1, step 6 except the amine hydrobromide N-3-piperazinocarbonylpropionyl)thyroxine methyl ester hydrobromide from step 4 was reacted with succinic anhydride. This material was purified by column chromatography (SiO$_2$).

$^1$H NMR(CDCl$_3$)δ 2.5–2.75(m, 8H, 2×CH$_2$CH$_2$), 2.9–3.2 (m, 2H, CH$_2$), 3.45–3.75(m, 8H, pip H's), 3.75(s,3H,CH$_3$), 4.8(m, 1H,CH), 6.9(m, 1H,NH), 7.1&7.65(s,4H,Ar H's).

Step 6 N-{3-[4-(3-Succinimidoxycarbonylpropionyl)piperazinocarbonyl]propionyl}thyroxine Methyl Ester. Reaction of the acid from step 5 with N-hydroxysuccinimide This material was prepared using the procedure outlined in Intermediate Preparation 1, step 7 except the acid N-{3-[4-(3-carboxypropionyl)piperazinocarbonyl]propionyl}thyroxine monoethyl ester from step 5 was used. This material was purified by column chromatography (SiO$_2$).

$^1$H NMR (CDCl$_3$) δ 2.5–2.8(m, 6H, 3×CH$_2$),2.8 ( s, 4H, suc CH$_2$CH$_2$), 2.9–3.2 (m, 4H, ArCH$_2$ & CH$_2$CO$_2$), 4.8 (m, 1H, CH), 6.8(d, 1H, NH), 7.1&7.65(s,4H, Ar H's).

Intermediate Preparation 4:
N-{4-[4-(4-Succinimidoxycarbonylbutyryl)piperazinocarbonyl] butyryl}thyroxine Methyl Ester

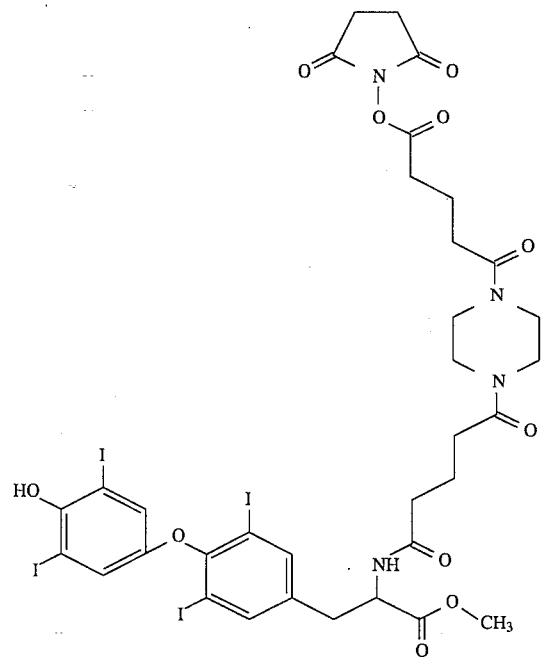

Step 1 N-(4-Carboxybutyryl)thyroxine Monomethyl Ester. Reaction of the amine from Intermediate Preparation 1, step 1 with glutaric anhydride This material was prepared using the procedure outlined in Intermediate Preparation 1, step 2 except glutaric anhydride was used in place of diglycolic anhydride.

$^1$H NMR(DMSO$_{d6}$)δ 1.6 (m, 2H, CCH$_2$C), 2.0– 2.2 (m, 4H, CH$_2$CCH$_2$), 2.75–3.1(m, 2H,ArCH$_2$), 3.6(s,3H, CH$_3$), 4.45 (m, 1H, CH), 7.0&7.8(s,4H,Ar H's), 8.35(d, 1H, NH).

Step 2 N-(4-Succinimidoxycarbonylbutyryl)thyroxine Methyl Ester. Reaction of the acid from step 1 with N-hydroxysuccinimide This material was prepared using the procedure outlined in Intermediate Preparation 3 except the acid N-(4-carboxybutyryl)thyroxine monomethyl ester from step 1 was used.

$^1$H NMR (CDCl$_3$)δ 2.15(m, 2H, CCH$_2$C), 2.38 (m, 2H,NHCOCH$_2$C), 2.65 (m, 2H, CCH$_2$CO$_2$), 2.85(s,4H, CH$_2$CH$_2$), 2.9–3.15(m, 2H, ARCH$_2$), 3.78(s,3H,CH$_3$), 4.82(m, 1H,CH), 6.5(d, 1H,NH), 7.1–7.65(s,4H,Ar H's).

Step 3 N-{4-[4-(Benzyloxycarbonyl)piperazinocarbonyl] butyryl}thyroxine Methyl Ester. Reaction of reactive ester from step 2 with benzyl 1-piperazinecarboxylate This material was prepared using the procedure outlined in Intermediate Preparation 1, step 4 except the reactive ester N-(4-succinimidoxycarbonylbutyryl)thyroxine methyl ester from step 2 was used. This material was purified using column chromatography (SiO$_2$).

$^1$H NMR(CDCl$_3$)δ 1.95(m, 2H,CCH$_2$C), 2.3– 2.5 (m, 4H, CH$_2$CCH$_2$), 2.95–3.2 (m, 2H,ArCH$_2$), 3.4– 3.65(m, 8H,pip H's), 3.78(s,3H,CH$_3$), 4.8(m, 1H,CH), 6.6(d, 1H,NH), 7.1&7.65(s,4H,Ar H's).

Step 4 N-(4-piperazinocarbonylbutyryl)thyroxine Methyl Ester. Treatment of the protected amine from step 3 with 30% HBr/HOAc This material was prepared using the procedure outlined in Intermediate Preparation 1, step 5 except the protected amine N-{4-[4-(Benzyloxycarbonyl)piperazinocarbonyl]butyryl}thyroxine methyl ester from step 3 was used.

Step 5 N-{4-[4-(4-Carboxybutyryl)piperazinocarbonyl]butyryl}thyroxine Monomethyl Ester. Treatment of the amine hydrobromide from step 4 with glutaric anhydride This material was prepared using the procedure outlined in Intermediate Preparation 1, step 6 except glutaric anhydride was reacted with N-(4-piperazinocarbonylbutyryl)thyroxine methyl ester hydromide from step 4. This compound was purified by column chromatography (SiO$_2$).

$^1$H NMR (CDCl$_3$)δ 1.95(m, 4H,2×CCH$_2$C), 2.3– 2.5(m, 8H,2×CH$_2$CCH$_2$), 2.9–3.2(m, 2H,ArCH$_2$), 3.4– 3.7(m, 8H,pip H's), 3.78(s,3H,CH$_3$), 4.8(m, 1H,CH), 6.7 (d, 1H,NH), 7.05&7.65(s,4H,Ar H's).

Step 6. N-{4-[4-(4-Succinimidoxycarbonylbutyryl)piperazinocarbonyl]butyryl}thyroxine Methyl Ester. Reaction of the acid from step 5 with N-hydroxysuccinimide This material was prepared using the procedure outlined in Intermediate Preparation 1, step 7 except the acid N-{4-[4-(4-carboxybutyryl)piperazinocarbonyl]butyryl}thyroxine monomethyl ester from step 5 was used. This compound was purified by column chromatography ( SiO$_2$).

$^1$H NMR(CDCl$_3$ )δ 1.95 (m, 2H, CCH$_2$CCO$_2$), 2.1(m, 2H,CCH$_2$CCON), 2.2–2.6(m, 6H, CH$_2$CCH$_2$, NCOCH$_2$CCH$_2$), 2.75 (m, 2H, CH$_2$CCH$_2$CO$_2$), 2.82 (s,4H, CH$_2$CH$_2$), 2.9–3.2 (m, 2H,ArCH$_2$), 3.4– 3.7 (m, 8H,pip H's), 3.78(s,3H,CH$_3$), 4.8(m, 1H,CH), 6.6(d, 1H,NH), 7.1&7.65(s,4H,Ar H's).

Preparation of Labeled Thyronine Hapten Analogues

Representative labeled thyronine hapten analogues were prepared from the above thyronine hapten analogues according the following procedures. The dry dimethyl sulfoxide used in the label preparation Examples was Aldrich #27, 685-5. All of the reactions involving thyroxine were performed under yellow lights.

Comparative Preparative Example:
Preparation of Label A

Preparation of HRP (Horseradish Peroxidase) labeled N-(Succinimidoxycarbonylmethoxyacetyl)thyroxine Methyl Ester from step 3 of Intermediate Preparation 1 (Label A).

This preparation is for comparison and is not an example used in the immunoassay of the invention.

The thyroxine hapten from step 3 of Intermediate Preparation 1 (49 mg) was dissolved in 2.176 mL dry dimethyl sulfoxide (DMSO). This solution (200 μl ) was brought to a final volume of 1.0 mL in DMSO.

A solution of horseradish peroxidase (HRP) was prepared in N-(2-hydroxyethyl)piperazine-N'-(3-propanesulfonic acid) buffer (EPPS, 0.1 M, pH 8). This solution was diluted to obtain a final concentration of 9.0 mg/mL following determination of the protein absorbance at 403 nm. (A$_{403}$1 mg/mL=2.24)

The HRP solution (1 mL) was combined with 500 μL of DMSO added dropwise with vortexing and was placed in a shaker which was set to a speed of 2400 rpm at room temperature for 15 minutes. The thyroxine hapten solution described above which was prepared immediately before use (500 μL) was added to the HRP dropwise with vortex mixing so that the molar ratio of thyroxine/HRP was 10/1. The reaction was returned to the shaker described above and was incubated for 4 hours. The reaction was placed in Spectrapor #2 dialysis tubing along with an additional 1 mL of 3-morpholinopropanesulfonic acid (MOPS, 0.2 M, pH 7) used to rinse the reaction container.

The reaction was dialyzed against 3 L of 0.2 M MOPS, pH 7, for 16 hours at 8° C. The dialysis buffer described above was changed 3 times more with at least 4 hours between buffer changes. Following dialysis, the sample was filtered through a 0.8 μm Millipore filter, merthiolate was added to a concentration of 0.02% as a preservative, and the label was stored refrigerated.

Invention Preparative Example 1
Preparation of Label B

N-[4-(3-Succinimidoxycarbonylpropionyl)piperazinocarbonylmethoxyacetyl] thyroxine Methyl Ester-HRP (Label B)

Succinimidoxycarbonylpropionyl)piperazinocarbonylmethoxyacetyl]thyroxine methyl ester from Intermediate Preparation 1 (19.3 mg) was dissolved in 1.332 mL DMSO. This solution (217 μL) was added to 325 μL DMSO.

A solution of HRP was prepared in 0.1 M EPPS buffer, pH 8. This solution was diluted to obtain a final concentration of 10.0 mg/mL following determination of the protein absorbance at 403 nm.

The HRP solution (1 mL) was combined with 500 μL of DMSO added dropwise with vortexing and was then placed in a shaker set at 2400 rpm at room temperature. The shaking was continued for about 30 minutes. The thyroxine hapten solution described above which was prepared immediately before use (500 μL) was added to the HRP dropwise with vortexing so that the molar ratio of thyroxine/HRP was 10/1. The reaction was returned to the shaker described above and was incubated for 4 hours. The reaction was placed in Spectrapor #2 dialysis tubing along with 1 mL of dialysis buffer used to rinse the reaction container.

The reaction was dialyzed against 3 L of 0.02 M MOPS, pH 7, for 16 hours at 8° C. The dialysis buffer described above was changed 3 times more with at least 4 hours between buffer changes. Following dialysis, the sample was filtered through a 0.8 μm Millilpore filter. Merthiolate was added to a concentration of 0.02% as a preservative, and the label was stored refrigerated.

Invention Preparative Example 2
Preparation of Label C

N-[4-(Succinimidoxycarbonylmethoxyacetyl)piperazinocarbonylmethoxyacetyl]thyroxine Methyl Ester-HRP N-[4-(Succinimidoxycarbonylmethoxyacetyl)piperazinocarbonylmethoxyacetyl] thyroxine methyl ester (18.4 mg) from Intermediate Preparation 2 was dissolved in 1.225 mL DMSO. This solution (217 μL) was added to 325 μL DMSO.

A solution of HRP was prepared in 0.1 M EPPS buffer, pH 8. This solution was diluted to obtain a final concentration of 10.0 mg/mL following determination of the protein absorbance at 403 nm.

The HRP solution (1 mL) was combined with 500 μL of DMSO added dropwise with vortexing and was then placed in a shaker set at 2400 rpm at room temperature. The shaking was continued for about 30 minutes. The thyroxine hapten solution described above which was prepared immediately before use (500 μL) was added to the HRP dropwise with vortexing so that the molar ratio of the thyroxine/HRP was 10/1. The reaction was returned to the shaker described above and was incubated for 4 hours. The reaction was placed in Spectrapor #2 dialysis tubing along with 1 mL of dialysis buffer used to rinse the reaction container.

The reaction was dialyzed against 3 L of 0.02 M MOPS, pH 7, for 16 hours at 8° C. The dialysis buffer described above was changed 3 times more with at least 4 hours between buffer changes. Following dialysis, the sample was filtered through a 0.8 μm Millipore filter. Merthiolate was added to a concentration of 0.02% as a preservative, and the label was stored refrigerated.

Invention Preparative Example 3
Preparation of Label D

N-{3-[4-(3-Succinimidoxycarbonylpropionyl)piperazinocarbonyl]propionyl}-thyroxine Methyl Ester-HRP (Label D)

N-{3-[4-(3-Succinimidoxycarbonylpropionyl)piperazinocarbonyl]propionyl}thyroxine methyl ester from Intermediate Preparation 3 (5.8 mg) from Intermediate Preparation 3 was dissolved in 1 mL DMSO.

A solution of HRP was prepared in 0.1 M EPPS buffer, pH 8. This solution was diluted to obtain a final concentration of 10.0 mg/mL following determination of protein absorbance at 403 nm.

The HRP solution (1 mL) was combined with 500 μL DMSO added dropwise with vortexing and was rotated end over end at room temperature for 20 minutes. The thyroxine hapten solution described above which was prepared immediately before use (500 μL) was added to the HRP dropwise with vortexing so that the molar ratio of thyroxine/HRP was 10/1. The reaction vial was covered with foil and was rotated end over end at room temperature for 4 hours. The reaction was placed in Spectrapor #2 dialysis tubing along with 500 μL of dialysis buffer used to rinse the reaction container.

The reaction was dialyzed against 3 L of 0.02 M MOPS, pH 7, for 16 hours at 8° C. The dialysis buffer described above was changed 3 times more with at least 4 hours between buffer changes. Following dialysis, the sample was filtered through a 0.22 μm Millipore filter. Merthiolate was added to a concentration of 0.02% as a preservative, and the label was stored refrigerated.

Invention Example 1:
Comparison of Thyroxine-HRP from Extended Piperazine Linkers (Label B & Label C)

Immobilized antibody beads were prepared by covalently attaching a thyroxine monoclonal antibody (Beckman T4AS12) to carboxyl group-containing beads of poly[styrene-co-3-(p-vinylbenzylthio)propionic acid](molar ratio 97.6/2.4; weight ratio 95/5) using [1-(1pyrolidinylcarbonyl)pyridinium chloride] as the activating agent. The copolymers were prepared according to the procedures described in Ponticello et al., U.S. Ser. No. 539,774, filed Jun. 18, 1990. The antibody was immobilized as described in Danielson and Specht, U.S. Ser. No. 539,680, filed Jun. 18, 1990.

The ability of immobilized thyroxine antibody to bind thyroxine-HRP labels was determined as indicated below:

The antibody beads were serially diluted with PBS (phosphate buffered saline, pH 7.4) containing 0.1% bovine gamma globulin (BGG) and 0.87 mM 8-anilino-1-naphthalenesulfonic acid ammonium salt (ANS) to give concentrations between 2000 and 0.63 nM antibody binding sites. The bead dilutions were mixed with equal volumes of thyroxine-HRP labels at $10 \times 10^{-11}$ M. Following a 1 hour incubation, the beads were pelleted by centrifugation. A sample of the supernatant was mixed with 100 μl of substrate (o-phenylenediamine/$H_2O_2$). The rates of color development at 450 nm were compared with those of standards to calculate the amount of thyroxine-HRP label remaining in solution. The amount of label bound to immobilized antibody at the highest antibody concentration tested (1000 nM binding sites) is reported.

| Label | % Label Bound at 1000 nM Binding Sites |
|---|---|
| B | 63 |
| C | 61 |

High fractions of both of the labels tested were bound by immobilized antibody.

Invention Example 2:
Immunocompetence of thyroxine HRP Conjugate Prepared from an Extended Piperazine Linker (Label D)

The ability of immobilized thyroxine antibody to bind label D was determined as described in invention example 1. The amount of label bound to immobilized antibody at the highest concentration tested (1000 nM binding sites) is reported.

| Label | % Label Bound at 1000 nM Binding Sites |
|---|---|
| D | 78 |

A high fraction of the label tested was bound by immobilized antibody.

Invention Example 3:
Comparison of Thyroxine HRP Conjugate Having a Glycolate Linker (Label A) With Conjugate (Label D) having a Piperazine Linker.

The ability of immobilized thyroxine antibody (Ab1) to bind labels A and D was determined as described in invention example 1. The amount of immobilized antibody binding sites required to bind 50% of a fixed concentration of these labels ($5 \times 10^{-11}$ M final concentration) is reported. A second thyroxine antibody (Ab2, T7-3.1, prepared at Kodak) was also evaluated in this experiment.

| Label | Binding Sites Required to Bind 50% of the Label | |
|---|---|---|
| | Ab1 | Ab2 |
| A | $7 \times 10^{-8}$M | $1 \times 10^{-6}$M |
| D | $3 \times 10^{-8}$M | $3 \times 10^{-7}$M |

These results show that the conjugate prepared from the extended piperazine linker binds more tightly to the two immobilized thyroxine antibodies.

The immunoassay of this invention can be carried out in solution or on dry analytical elements. It is convenient to carry the assay out on the dry elements. The elements can be single or multilayer or a combination of layers having zones within such layers. In general the elements can comprise a radiation transmissive support, one or more reagent layers, a particulate spreading layer preferably comprising beads upon which antibodies to the particular thyronine are immobilized.

The layers can be coated using well known coating techniques in this art. For example slide-extrusion hoppers of the type described in U.S. Pat. No. 2,761,417 are often advantageous for simultaneous coating of a plurality of layers at least one of which is comprised of polymeric particles bearing immobilized antibody beads. More particularly, a multilayer element can be coated by directing a coating composition containing the beads through an extrusion slot of a slide extrusion hopper and simultaneously flowing a layer of a second coating composition, which, if desired, may also contain beads down a slide surface of the slide-extrusion hopper.

The particulate layer in which the thyronine antibodies are immobilized is porous. Materials for use in such layers are well known in the art of making dry analytical elements. A preferred particulate layer is a bead spreading layer (BSL). This layer can be easily constructed to have suitable porosity for use in the elements of the present invention to accommodate a test sample (e.g. 1 to 100 μL), diluted or undiluted. Preferably, the spreading layer is isotropically porous, which property is created by interconnected spaces between the particles comprising the zone. By isotropically porous is meant that the spreading layer uniformly spreads the applied fluid radially throughout the layer.

Useful particulate spreading layers, including bead spreading layers are disclosed in U.S. Pat. Nos. 4,670,381; 4,258,001 and 4,430,436.

The particulate layer of the element is carried on a suitable support. Such a support can be any suitable dimensionally stable, and preferably, nonporous and transparent (i.e. radiation transmissive) material which transmits electromagnetic radiation of a wavelength between about 200 and about 900 nm. A support of choice for a particular element should be compatible with the intended mode of detection (reflection, transmission or fluorescence spectroscopy). Useful support materials include polystyrene, polyesters [e.g. poly(ethylene terephthalate)], polycarbonates, cellulose esters (e.g. cellulose acetate), etc.

The element can comprise one or more additional layers, e.g. separate or combined reagent/spreading layer and a gelatin/buffer layer containing other necessary additives, coupling enzymes, etc.

The gelatin/buffer layer or the reagent layer or the spreading layer of the element can contain the indicator composition comprising one or more reagents dispersed in one or more synthetic or natural binder materials, such as gelatin, or other naturally occurring colloids, homopolymers and copolymers, such as poly (acrylamide) , poly(N-vinylpyrolidone), poly (N-isopropylacrylamide), poly (acrylamide-co-N-vinyl-2-pyrolidone) and similar copolymers.

Other optional layers, e.g. subbing layers, radiation-blocking layers, etc. can be included if desired. All layers of the element are in fluid contact with each other, meaning that fluids and reagents and uncomplexed reaction products in the fluids can pass between superposed regions of adjacent layers.

The layers of the element can contain a variety of other desirable but optional components, including surfactants, thickeners, buffers, hardeners, antioxidants, coupler solvents, and other materials known in the art. The amounts of these components are also within the skill of a worker in the art.

The elements can be used to determine low concentrations of thyronines in a liquid, such as a biological fluid (e.g., whole blood, serum, plasma, urine, spinal fluid, suspensions of human or animal tissue, feces, saliva, lymphatic fluid and the like). The thyronine, particularly thyroxine can be determined at concentrations as low as about $10^{-15}$ molar, and most generally at a concentration of from about $10^{-10}$ to about $10^{-4}$ molar.

The assay can be carried out using any suitable label which can be attached to the defined thyronine derivatives. Useful labels include radioactive tags, dyes, fluorescers, enzymes, enzyme substrates, enzyme inhibitors, allosteric effectors, cofactors and other known enzyme modulators. Enzymes, such as glucose oxidase, peroxidases such as horseradish peroxidase and amine-enriched horseradish peroxidase, alkaline phosphatase and galactosidase are preferred labels.

When an enzyme label is used, the substrate for the enzyme is present in the element or added thereto in the developing liquid. The substrate can be added to the element prior to or simultaneously with the liquid sample, or after completion of the binding reaction. It is within the skill of the ordinary worker in clinical chemistry to determine a suitable substrate for a given label. The substrate can be a material which is directly acted upon by the enzyme label, or a material that is involved in a series of reactions which involve enzymatic reaction of the label. For example, if the enzyme label is a peroxidase, the substrate is hydrogen peroxide. Using glucose oxidase as an example, the substrate glucose is generally present in the reagent layer or is added in the developing liquid to yield about 0.01 moles/m$^2$, and preferably from about 0.001 to about 0.1 mole/m$^2$. A worker skilled in the art would know how to adjust the amount of a particular substrate for the amount of enzyme label used in the assay.

When certain labels are used, e.g. enzymes, cofactors, enzyme substrates or enzyme modulators, the reagent layer contains an indicator composition comprising one or more reagents which provide a detectable species as a result of reaction of the label. Preferably, the indicator composition is a colorimetric indicator composition which provides a colorimetrically detectable species as a result of enzymatic reaction of an enzyme-labeled ligand analog with a substrate.

The indicator composition can be a single compound which produces a detectable dye upon enzymatic reaction, or a combination of reagents which produce the dye. For example, when glucose is used as the substrate and glucose oxidase as the enzyme label, the colorimetric indicator composition can include a coupler and oxidizable compound which react to provide a dye. Alternatively, the composition can include a leuco dye and peroxidase or another suitable peroxidative compound which generate a detectable dye as a result of the formation of hydrogen peroxide produced when glucose oxidase converts glucose to gluconic acid. Useful leuco dyes are known in the art and include those, for example, described in U.S. Pat. No. 4,089,747 (issued May 16, 1978 to Bruschi) and U.S. Ser. No. 612,509, filed May 21, 1984 by Babb et al. The particular amounts of the colorimetric indicator composition and its various components are within the skill of a worker in the art.

The immunoassay can be manual or automated. In general, the amount of a ligand in a liquid is determined by taking the element from a supply roll, chip packet or other source and physically contacting a finite area of the spreading layer with a sample of the liquid, e.g. 1 to 100 μl. The finite area which is contacted is generally no more than about 100 mm$^2$.

The amount of ligand is determined by passing the element through a suitable apparatus for detecting the complexed ligand analog directly or the detectable species formed as a result of enzymatic reaction of an enzyme label and a substrate. For example, the species can be detected with suitable radiometric, fluorometric or spectrophotometric apparatus using generally known procedures. In an enzymatic reaction, the resulting product is determined by measuring, for example, the reflection or transmission density or fluorescence in the center of the finite area which was contacted with the test sample. The area which is measured is generally from about 3 to about 5 mm in diameter for competing assays. The amount of ligand in the liquid sample is inversely proportional to the amount of label measured in the center of the finite area. In a preferred embodiment a separate developer step is required in order to maximize separation of complexed ligand from uncomplexed ligand. Generally, label measurement is carried out after from about 5 to about 180 seconds after sample contact and spreading or application of the developing liquid.

The following examples demonstrate the utility of the labeled thyronine derivatives in carrying out immunoassays conveniently on dry immunoassay elements. In each of the examples utility is demonstrated with thyroxine embodiments of thyronine derivatives.

In the following examples the assay procedures were carried out step-wise according to the following protocol. Ten μL of a sample was spotted on the top surface of a dry immunoassay element of the invention. The element with the now spotted sample was then incubated at 37° C. for 5 minutes. It is expected that with the elements of this invention equilibrium in the competition between labeled and unlabeled ligand for receptor binding sites in the bead spreading layer will be complete after no more than 5 minutes. After this period of incubation the element was removed from the incubator and developed with 10 uL of enzyme substrate solution. For the assays used in the examples the label is horseradish peroxidase (HRP) and the substrate used in the developing solution is about 0.03% by weight $H_2O_2$. The developing solution also contains sodium phosphate buffer (pH 6.8) 0.01M, 4'-hydroxyacetanilide (electron transfer agent) 0.005M, diethylenetriaminepentacetic acid 10 μM and a surfactant. The developing solution causes development of the detectable species. The bound HRP-labeled ligand catalyzes the oxidation of a colorless leuco dye to its colored form. Such dyes are well known in the dry analytical element art and will not be described in detail here. In the examples presented herein the leuco dye is a triarylimidazole. The rate of the catalyzed reaction is measured from the change in reflection density over time at 37° C. Methods and means for measuring reflection density are well known in the analytical arts.

Invention Example 4:

This example demonstrates the preparation of an analytical element and the use of the element with a novel labeled thyronine hapten analogue in a competitive binding immunoassay to detect thyroxine.

The element was prepared using known technology to have the following structure:

|  |  | Coverage (g/m2) |
|---|---|---|
| Spreading Layer | Immobilized T7-3.1 Antibody (see Example 1 for preparation) | 0.1 |
|  | Particles of poly[m- & p-vinyl-toluene (64:36)-co-methacrylic acid](92:2 weight ratio) (30 μm) | 130 |
|  | 4,5-bis(4-dimethylaminophenyl)-2-(4-hydroxy-3,5-dimethoxyphenyl)-imidazole leuco dye | 0.2 |
|  | poly(methyl acrylate-co-sodium 2-acrylamido-2-methylpropane-sulfonate-co-2-acetoacetoxyethyl methacrylate (90:4:6 weight ratio) | 2.58 |
|  | N-[tris(hydroxymethyl)methyl]-2-aminoethanesulfonic acid (pH 7.0) | 0.219 |
|  | 5,5-dimethyl-1,3-cyclohexanedione | 1.8 |
|  | Zonyl FSN nonionic surfactant (DuPont) | 0.054 |
|  | 4'-hydroxyacetanilide | 0.15 |
|  | Methanol | 0.675 |
| Gelatin Layer | hardened gelatin | 10 |
|  | 4'-hydroxyacetanilide | 0.15 |
|  | N-[tris(hydroxymethyl)methyl]-2-aminoethanesulfonic acid (pH 7.0) | 0.68 |
|  | Triton X-100 nonionic surfactant (Rohm & Haas) | 0.02 |
|  | 5-(Aminosulfonyl)-4-chloro-2-[(2-furanylmethyl)amino]benzoic acid) | 0.166 |
| Support | Poly(ethylene terephthalate) |  |

A series of human serum based calibrators containing thyroxine and a thyroxine-HRP label (Label B from preparative invention example 1 or Label D from preparative invention example 3) were prepared. The thyroxine-HRP labels could have also been included in a layer or zone of the element. The concentration of thyroxine varied from 0.25 to 31.1 μg/dL. The thyroxine-HRP label was added to give a final concentration of 1.5 nM. The series of thyroxine standards (10 μL aliquots) was spotted onto the spreading layers of a series of analytical elements. After 5 minutes incubation at 37° C., a wash solution (10 μL) comprising hydrogen peroxide (0.03%), sodium phosphate buffer (0.01 M, pH 6.8), 4'-hydroxyacetanilide (5 mM), diethylenetriaminepentaacetic acid (10 μM) and hexadecylpyridinium chloride (0.1%) was added to wash unbound complex away from the detection zone and to initiate dye formation. After about 40 seconds, the reflection density ($D_r$) was measured at the center of the area at 680 nm at 37° C. The $D_r$ values were converted to Dt by the Clapper-Williams transform. The change in $D_t$ over 60 seconds was calculated. The results are shown below:

|  | Rate (Dt/min) | |
|---|---|---|
| Thyroxine, g/dl | Label B | Labal D |
| 0.25 | 0.0646 | 0.05803 |
| 3.2 | 0.0482 | 0.04836 |
| 9.1 | 0.0359 | 0.03411 |
| 31.1 | 0.0200 | 0.02141 |

These results show that there is a significant change in rates over the desired dynamic range for both of the extended piperazine linker labels tested.

The invention has been described in detail with particular reference to preferred embodiments thereof, but it will be understood that variations and modifications can be effected within the spirit and scope of the invention.

What is claimed is:

1. An immunoassay for a thyronine derivative comprising:
  A. contacting a liquid sample, containing a thyronine derivative, with a labeled thyronine hapten analogue of the derivative in the presence of antibodies for the thyronine derivative under conditions that promote the formation of antibody-thyronine immunocomplexes; and
  B. determining the bound or unbound quantity of the thyronine derivative in the liquid; characterized in that the labeled thyronine derivative comprises:
    (1) a label, of the type used in immunoassays, having an amine or sulfhydryl group;
    (2) a thyronine nucleus; and
    (3) a linking chain, linking the thyronine nucleus to the label through the amino or the carboxyl group of the thyronine nucleus and the amine or sulfhydryl group of the label, said linking chain having therein from 4 to about 22 chain atoms, and comprising at least one ring group selected from 1,4-piperazinylene; 2,5-dimethyl-1,4-piperazinylene; 1,3-imidazolidinylene;

and 1,3-hexahydrodiazepinylene; and one or more $C_1$ to $C_6$ alkylene groups; wherein, said ring group and said alkylene groups are interconnected to each other through one or more groups selected from —O—, —S—, imino, amide, carboxyl and carbonyl.

2. The immunoassay of claim 1 wherein the labeled thyronine hapten analogue conforms to the structure:

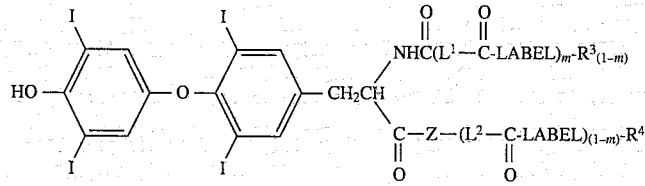

wherein —Z— represents 1,4-piperazinylene, 2,5-dimethyl-1,4-piperazinylene, 1,3-imidazolidinylene, 1,3-hexahydrodiazepinylene, 1,4-piperazinylenecarbonyl, 2,5-dimethyl-1,4-piperazinylenecarbonyl, 1,3-imidazolidinylenecarbonyl, 1,3-hexahydrodiazepinylenecarbonyl, oxa (—O—), thia (—S—) or imino (—$NR^1$—) in which $R^1$ is hydrogen or alkyl of about 1 to 6 carbon atoms;

$L^1$ and $L^2$ each represent a linking chain having therein from 4 to about 22 chain atoms, including (i) at least one ring group selected from the group consisting of 1,4-piperazinylene; 2,5-dimethyl-1,4-piperazinylene; 1,3-imidazolidinylene; and 1,3-hexahydrodiazepinylene; and (ii) one or more $C_1$ to $C_6$ alkylene groups; wherein the groups (i) and (ii) are interconnected to each other through one or more groups selected from the group consisting of —O—, —S—, imino, carbonyl, amide (—$OCNR^1$— and —$NR^1CO$—), and ester (—COO— and —OCO—);

$R^3$ represents alkyl, hydroxyalkyl, or alkoxy of about 1 to 10 carbon atoms; and $R^4$ is alkyl of about 1 to 10 carbon atoms; and m is 0 or 1.

3. The immunoassay of claim 1 or 2 wherein the linking chain of the labeled thyronine hapten analogue includes a 1,4-piperazinylene group and one or more oxa, carbonyl, imino and amide groups.

4. The immunoassay of claim 1 or 2 wherein the nucleus of the labeled thyronine hapten analogue is thyroxine.

5. The immunoassay of claim 2 wherein $L^1$ in the labeled thyronine hapten analogue includes a 1,4-piperazinylene ring group and one or more $C_1$ to $C_6$ alklene groups interconnected to each other through one or more oxa, carbonyl, imino, and amide groups.

6. The immunoassay of claim 2 wherein the labeled thyronine hapten analogue is selected from the group consisting of:
N-[4-(3-HRP-carbonylpropionyl)piperazinocarbonylmethoxyacetyl]thyroxine methyl ester;
N-[4-(HRP-carbonylmethoxyacetyl)piperazinocarbonylmethoxyacetyl]thyroxine methyl ester;
N-{3-[4-(3-HRP-carbonylpropionyl)piperazinocarbonyl]propionyl}thyroxine methyl ester; and
N-{4-[4-(4-HRP-carbonylbutyryl)piperazinocarbonyl]butyryl}thyroxine methyl ester.

7. The immunoassay of claim 2 wherein $L^1$ in the labeled thyronine hapten analogue is selected from the group consisting of:
methyleneoxymethylenecarbonyl-1,4-piperazinylene-carbonylethylene;
methyleneoxymethylenecarbonyl-1,4-piperazinylene-carbonylmethyleneoxymethylene;
ethylenecarbonyl-1,4-piperazinylenecarbonylethylene and
trimethylenecarbonyl-1,4-piperazinylenecarbonyl-trimethylene.

8. An immunoassay element having a layer, zone or coating of a labeled thyronine hapten drug analogue described in any one of claims 1, 2, 5, 6 or 7.

9. The immunoassay of claim 2 wherein m is 1.

* * * * *